US012636630B2

(12) United States Patent
Williams et al.

(10) Patent No.: US 12,636,630 B2
(45) Date of Patent: May 26, 2026

(54) SYSTEM AND METHOD FOR COOLING A METHANOL REACTOR EFFLUENT VAPOR STREAM IN METHANOL PRODUCTION PLANT

(71) Applicant: L'Air Liquide, Societe Anonyme pour l'Etude et l'Exploitation des Procedes Georges Claude, Paris (FR)

(72) Inventors: Bryce Williams, Frankfurt am Main (DE); Tobias Oelmann, Frankfurt am Main (DE)

(73) Assignee: L'Air Liquide, Societe Anonyme Pour l'Etude et l'Exploitation des Procedes Georges Claude, Paris (FR)

( * ) Notice: Subject to any disclaimer, the term of this patent is extended or adjusted under 35 U.S.C. 154(b) by 686 days.

(21) Appl. No.: 18/099,472

(22) Filed: Jan. 20, 2023

(65) Prior Publication Data

US 2023/0264162 A1     Aug. 24, 2023

(51) Int. Cl.
    *B01J 19/00* (2006.01)
    *B01D 5/00* (2006.01)
    *C07C 29/78* (2006.01)
(52) U.S. Cl.
    CPC ........ *B01J 19/0013* (2013.01); *B01D 5/0027* (2013.01); *B01D 5/0087* (2013.01);
    (Continued)
(58) Field of Classification Search
    CPC ...... B01D 5/00; B01D 5/0027; B01D 5/0078; B01D 5/0087; B01J 4/00–002; B01J 19/00; B01J 19/0006; B01J 19/0013;

B01J 2219/00; B01J 2219/00049; B01J 2219/00051; B01J 2219/00074; B01J 2219/00087; B01J 2219/00092; B01J 2219/00105; B01J 2219/0011; B01J 2219/00121; B01J 2219/0013;
(Continued)

(56) References Cited

U.S. PATENT DOCUMENTS 7,115,670 B2 * 10/2006 Hensman ................. B01J 8/228
                                                          518/706
11,247,954 B2   2/2022 Oelmann et al.
(Continued)

OTHER PUBLICATIONS

Ullmann's Encyclopedia of Industrial Chemistry, Sixth Edition, 1998 Electronic Release, vol. 21, Chapter "Methanol," Sub-chapter 5.2 Synthesis, pp. 620-621.
(Continued)

*Primary Examiner* — Natasha E Young
(74) *Attorney, Agent, or Firm* — Elwood L. Haynes

(57)     ABSTRACT

Provided is a method for cooling a methanol r synthesis reactor effluent vapor stream in a methanol production plant, wherein the method comprises the steps of: receiving, using an inlet of a cooler, the methanol synthesis reactor effluent vapor stream from an interchanger or a methanol synthesis reactor of the methanol production plant; and spraying, using a recirculation pump connected to a spraying device, a liquid condensate received from a methanol synthesis loop onto a tube sheet of the cooler which enables direct contact of the liquid condensate with the methanol synthesis reactor effluent vapor stream and cools the methanol synthesis reactor effluent vapor stream.

18 Claims, 3 Drawing Sheets

(52) U.S. Cl.
CPC ..... *C07C 29/78* (2013.01); *B01J 2219/00092*
(2013.01); *B01J 2219/0013* (2013.01)

(58) Field of Classification Search
CPC ....... C07C 29/00; C07C 29/15; C07C 29/151;
C07C 29/74; C07C 29/76; C07C 29/78;
C07C 31/04
See application file for complete search history.

(56)                     References Cited

U.S. PATENT DOCUMENTS

2010/0160694 A1*   6/2010   Fitzpatrick .......... C07C 29/1516
568/913
2021/0078860 A1     3/2021   Mueller-Hagedorn

OTHER PUBLICATIONS

EP Search Report and Written Opinion for EP 22020065, mailed Jul.
1, 2022.

* cited by examiner

SYSTEM AND METHOD FOR COOLING A METHANOL REACTOR EFFLUENT VAPOR STREAM IN METHANOL PRODUCTION PLANT

CROSS REFERENCE TO RELATED APPLICATION

This application claims the benefit of priority under 35 U.S.C. § 119 (a) and (b) to European patent application No. EP220200065.3, filed Feb. 18, 2022, the entire contents of which are incorporated herein by reference.

FIELD OF THE INVENTION

The present disclosure relates generally to methanol production, specifically, to small-scale methanol production; more specifically, the present disclosure relates to a system and method for cooling a methanol reactor effluent vapor stream in a methanol production plant.

BACKGROUND OF THE INVENTION

Processes for the production of methanol by catalytic conversion of synthesis gas containing hydrogen and carbon oxides have long since been known to those skilled in the art. For example in Ullmann's Encyclopedia of Industrial Chemistry, Sixth Edition, 1998 Electronic Release, Chapter "Methanol", Sub-chapter 5.2 "Synthesis", various basic processes for the production of methanol are described.

A two-stage process for the production of methanol is known for example from EP 0 790 226 B1. The methanol is produced in a cyclic process in which a mixture of fresh and partly reacted synthesis gas first is supplied to a water-cooled reactor and then to a gas-cooled reactor, in each of which the synthesis gas is converted to methanol on a copper-based catalyst. The methanol produced in the process is separated by cooling, condensing and phase separation from the residual gas phase containing synthesis gas components like hydrogen ($H_2$) and carbon monoxide (CO) to be recirculated. The residual gas phase is counter-currently passed through the gas-cooled reactor as coolant and pre-heated to a temperature of 220 to 280° C., before it is introduced into the first methanol synthesis reactor. A part of the synthesis gas to be recirculated is removed from the process as purge stream, in order to prevent that inert components are enriched within the synthesis cycle. It is to be noted that such a methanol synthesis plant design aims primarily at high methanol production capacities of e. g. 5000 metric tons per day or even more.

A historic trend has been for the capacity of world-scale methanol plants to be designed for ever-higher capacities. The transition from 2000 metric tons per day to 5000 tons per day was significant. Current designs contemplate capacities up to 10,000 tons per day. Plants of higher capacity have considerable advantages because the cost of equipment becomes cheaper per unit product capacity. Typical equipment cost scales exponentially according to the following formula:

$$Cost2=Cost1\times(Size2/Size1)^0.65.$$

The exponent of 0.65 is typical, but other values are possible. The appropriate exponent will vary, depending on the type of equipment and the size range of that equipment. However, using this formula as written suggests that doubling the capacity would increase the cost by only a factor of 1.57 (=2^0.65). Thus, significant economies of scale are present at large capacities and the constraint to have more equipment items or larger equipment sizes is not severe for large capacity plants. In contrast, if a plant is designed for a smaller capacity, such as 1000, 500, or even less than 250 tons per day, a number of equipment items and a size of those items strongly affect the methanol production cost. In particular contrast to the large plants, air coolers are expensive to purchase and have high plot space requirements compared to cooling water coolers. Considering this, a designer is compelled to reduce the number of equipment items by eliminating the most expensive cooling units integrated with the system. Simply eliminating the air cooler and using a reasonable design of the interchanger gives a temperature of 120 degree Celsius (° C.) or more for an inlet gas to the cooler. Such a temperature is higher than typically allowed for process-compatible steel metallurgies in cooling water service where chlorides are present. Further, high metal surface temperatures can result in a breakdown of the cooling water treatment chemicals and give rise to corrosion on a process side and/or fouling on a cooling waterside. For example, when chlorides are present, such temperatures can cause corrosion and fouling on the cooling water side of the cooler. Chloride content when using stainless steel can cause stress corrosion cracking. Using higher-grade metallurgy or a lower chloride content can avoid the corrosion problem, but then the equipment or the cooling water supply becomes more expensive. Even in this case, the cooling water chemistry may still cause fouling in an exchanger even without corrosion.

In typical methanol processes, especially at large capacities (e.g. 5000 metric tons per day), the methanol synthesis loop includes a two-stage synthesis with a gas-cooled reactor (GCR) and water-cooled reactor (WCR). Interstage condensation is accomplished after the water-cooled reactor (WCR) with an interchanger and air cooler leading into a vapor-liquid separator to remove condensed product. Similarly, at the exit of the gas-cooled reactor (GCR), high-temperature boiler feed water is used followed by an interchanger, air cooler and finally, a cooling water cooler. A single-stage synthesis with a water-cooled reactor (WCR) typically comprises an interchanger, air cooler, and then, finally, a cooling water cooler. The key constraint is that various cooling steps are required before the use of the cooling water cooler. To achieve cost-effective production of methanol in small capacity plants, either from conventional syngas with a high concentration of carbon monoxide (CO) or from the combination of carbon dioxide ($CO_2$) and hydrogen with little or no CO, it is important to have a minimized equipment count. Furthermore, the cost of the underlying equipment must be also minimized.

Therefore, there is a need to address the aforementioned technical drawbacks in existing technologies for a cooling system that is suited to small-capacity methanol plants.

SUMMARY OF THE INVENTION

The present disclosure seeks to provide a system and method for cooling a methanol reactor effluent vapor stream in a small-scale methanol production plant where the capital costs (investment costs) are dominant in determining the overall economics. The present disclosure aims to provide a solution that overcomes, at least partially, the problems encountered in the prior art and provide an improved cooling system where, in an example, the primary air cooler is deleted from a classical methanol synthesis loop. A simple addition of a liquid spray using a recirculation pump and a spraying device onto the cooler inlet cools the incoming methanol synthesis reactor effluent vapor stream directly and also cools a tube sheet and other metal surfaces, thereby allowing the use of conventional materials without corrosion issue. The object of the present disclosure is achieved by the solutions provided in the enclosed independent claims. Advantageous implementations of the present disclosure are further defined in the dependent claims.

According to a first aspect, the present disclosure provides a cooling system for cooling a methanol synthesis reactor effluent vapor stream in a methanol production plant, wherein the cooling system is integrated with the methanol production plant, wherein the cooling system comprises:

a cooler, preferably a tube and shell heat exchanger, comprising cooling tubes for cooling the methanol synthesis reactor effluent vapor stream, a shell side for passing of a fluid cooling medium, a tube sheet for separating the cooling tubes from the shell side, and an inlet that receives the methanol synthesis reactor effluent vapor stream from an interchanger or from a methanol synthesis reactor of the methanol production plant; and a recirculation pump connected to a spraying device that is configured to spray a liquid condensate received from a methanol synthesis loop onto a tube sheet of the cooler which enables direct contact of the liquid condensate with the methanol synthesis reactor effluent vapor stream and cools the methanol synthesis reactor effluent vapor stream.

The cooling system for cooling the methanol synthesis reactor effluent vapor stream in the methanol production plant according to the present disclosure enables cost-effective production of methanol in small capacity plants, either from conventional syngas with a high CO content or from a combination of carbon dioxide ($CO_2$) and hydrogen, with little or no CO. The cooling system enables a single cooler to be used for cooling the methanol synthesis reactor effluent vapor stream instead of multiple cooling systems used in typical methanol processes, thus providing an economic advantage for small-scale methanol production facilities. The cooling system provides direct cooling of the methanol synthesis reactor effluent vapor stream with the recirculation pump with low head requirements onto the cooler inlet, and also cools the tube sheet, and other metal surfaces, allowing the use of conventional materials without corrosion issue and avoiding the problem of high inlet temperatures.

According to a second aspect, the present disclosure provides a method for cooling a methanol synthesis reactor effluent vapor stream in a methanol production plant, wherein the method comprises the steps of:

receiving, using an inlet of a cooler, the methanol synthesis reactor effluent vapor stream from an interchanger or from a methanol synthesis reactor of the methanol production plant, wherein the cooler is preferably a tube and shell heat exchanger and comprises cooling tubes for cooling the methanol synthesis reactor effluent vapor stream, a shell side for passing of a fluid cooling medium, a tube sheet for separating the cooling tubes from the shell side; and spraying, using a recirculation pump connected to a spraying device, a liquid condensate received from a methanol synthesis loop onto the tube sheet of the cooler which enables direct contact of the liquid condensate with the methanol synthesis reactor effluent vapor stream and cools the methanol synthesis reactor effluent vapor stream.

The method of cooling the methanol synthesis reactor effluent vapor stream in the methanol production plant according to the present disclosure is of advantage in that the method enables cost-effective production of methanol in small capacity plants, either from conventional syngas or from the combination of carbon dioxide ($CO_2$) and hydrogen. The method enables direct cooling of the methanol synthesis reactor effluent vapor stream with a simple liquid spray using the recirculation pump with low head requirements onto the cooler inlet, and also cools the tube sheet, and other metal surfaces, thereby allowing the use of conventional materials without issue and avoiding the problem of high inlet temperatures.

Embodiments of the present disclosure eliminate the aforementioned drawbacks in existing known approaches for cooling the methanol synthesis reactor effluent vapor stream in the methanol production plant. The advantage of the embodiments according to the present disclosure is that the embodiments enable cost-effective production of methanol in small capacity plants, either from conventional syngas or from the combination of $CO_2$ and hydrogen with a single cooler for cooling the methanol synthesis reactor effluent vapor stream instead of multiple cooling systems used in typical methanol processes, thus providing an economic advantage for small scale methanol production facilities. The cooling system avoids higher temperatures that presented the problem for the materials and cooling water chemicals in the cooler of the methanol synthesis loop by cooling the vapor stream via direct contact with the cooled liquid condensate.

Additional aspects, advantages, features, and objects of the present disclosure are made apparent from the drawings and the detailed description of the illustrative embodiments construed in conjunction with the appended claims that follow. It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. To illustrate the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, the same elements have been indicated by identical numbers. Embodiments of the present disclosure will now be described, by way of example only, with reference to the following diagrams wherein.

DETAILED DESCRIPTION OF THE INVENTION

Figure 1:
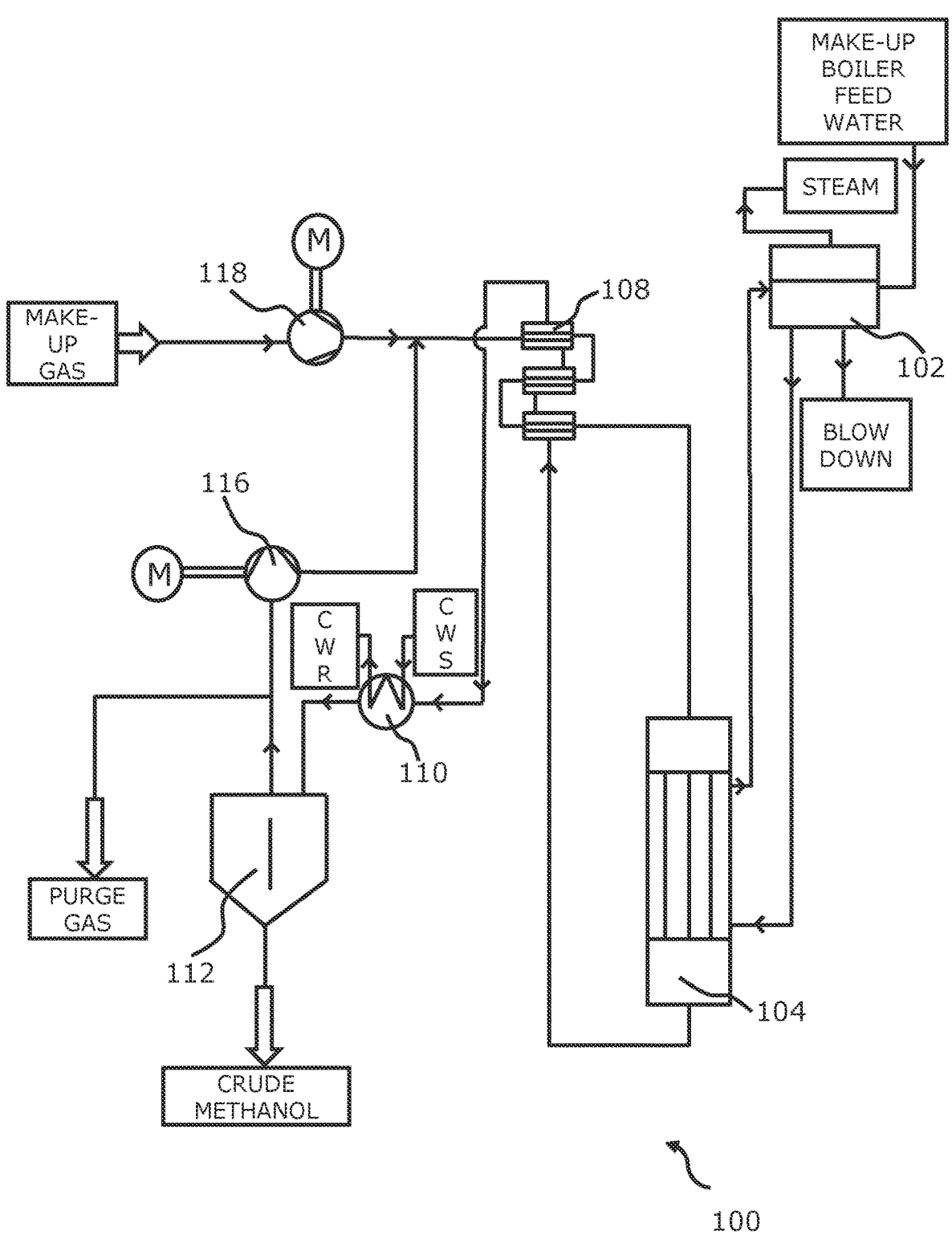
FIG. 1 is a schematic illustration of a single-stage methanol synthesis system according to the prior art with a water cooled reactor (WCR) without an air cooler for methanol production.

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

According to a first aspect, the present disclosure provides a cooling system for cooling a methanol synthesis reactor effluent vapor stream in a methanol production plant, wherein the cooling system is integrated with the methanol production plant, wherein the cooling system comprises: a cooler, preferably a tube and shell heat exchanger, comprising cooling tubes for cooling the methanol synthesis reactor effluent vapor stream, a shell side for passing of a fluid cooling medium, a tube sheet for separating the cooling tubes from the shell side, and an inlet that receives the methanol synthesis reactor effluent vapor stream from an interchanger or from a methanol synthesis reactor of the methanol production plant; and a recirculation pump connected to a spraying device that is configured to spray a liquid condensate received from a methanol synthesis loop onto a tube sheet of the cooler which enables direct contact of the liquid condensate with the methanol synthesis reactor effluent vapor stream and cools the methanol synthesis reactor effluent vapor stream.

The cooling system according to an aspect of the invention for cooling the methanol synthesis reactor effluent vapor stream in the methanol production plant according to the present disclosure enables cost-effective production of methanol in small capacity plants, either from conventional syngas, comprising CO and little or no $CO_2$, or from the combination of carbon dioxide ($CO_2$) and hydrogen. The cooling system enables a single cooler to be used for cooling the methanol synthesis reactor effluent vapor stream instead of multiple cooling systems used in typical methanol processes, thus providing an economic advantage for small-scale methanol production facilities. The cooling system provides direct cooling of the methanol synthesis reactor effluent vapor stream with a simple liquid spray using the recirculation pump with low head requirements at the cooler inlet. The cooling system also cools tube sheet, and other metal surfaces, thereby allowing the use of conventional materials without issue and avoiding the problem of high inlet temperatures. The recirculation pump is a small pump with low head requirements which further reduces the cost of the cooling system.

Optionally, according to an aspect of the invention, the liquid condensate spray cools metal surfaces of the cooler. The cooling of the metal surfaces relaxes the constraint of the material and improves the efficiency of the cooler.

Optionally, according to an aspect of the invention, the liquid condensate comprises a stabilized crude methanol, a product methanol, or a wastewater obtained from the methanol synthesis loop. The liquid condensate comprising the stabilized crude methanol, the product methanol, or the wastewater obtained from the methanol synthesis loop is cooled and used directly to cool the methanol reactor effluent vapor stream with no additional cooling equipment, e. g. a separate air cooler.

Optionally, according to an aspect of the invention, the liquid condensate is cooled to a temperature below about 50 degrees Celsius, more preferably below about 40 degrees Celsius. Experiments and/or calculation data have shown this temperatures to allow a safe and reliable condensation of the major part of the crude or raw methanol produced in the methanol synthesis reactor, while keeping the energy requirements at a tolerable level.

Optionally, according to an aspect of the invention, the spraying device is arranged at the inlet of the cooler. This allows a direct contact of the liquid condensate with the methanol synthesis reactor effluent vapor stream and thus cools the methanol synthesis reactor effluent vapor stream very effectively.

Optionally, according to an aspect of the invention, a mixture temperature of the sprayed liquid condensate and methanol synthesis reactor effluent vapor is below about 100 degrees Celsius, preferably below about 90 degrees Celsius. By lowering the mixture temperature to below these upper values, corrosion of the cooler internals and the downstream equipment is effectively prevented, especially when chlorides are present.

Optionally, the cooling system according to an aspect of the invention, further comprises a vapor-liquid separator for separating for separating a liquid condensate stream and a residual gas stream from the cooled methanol synthesis reactor effluent vapor stream. The crude methanol comprised in the liquid condensate stream is a raw methanol product in a mix with water and impurities. The residual gas is unreacted syngas that may comprise carbon monoxide (CO), methane, ethane, and dimethyl ether.

Optionally, according to an aspect of the invention, the cooler comprises an integrated vapor-liquid separator for separating a liquid condensate stream and a residual gas stream from the cooled methanol synthesis reactor effluent vapor stream. Such configuration has advantages for small capacity plants because the vapor-liquid separator is also eliminated as a separate equipment position.

Optionally, according to an aspect of the invention, the cooling system does not comprise an air cooler. Since the cooling of the methanol synthesis reactor effluent vapor stream is effected by the cooling system according to the invention, comprising the spraying of the liquid condensate onto the tube sheet of the cooler, the expensive air cooler can be omitted.

According to a second aspect, the present disclosure provides a method for cooling a methanol synthesis reactor effluent vapor stream in a methanol production plant, wherein the method comprises the steps of: receiving, using an inlet of a cooler, the methanol synthesis reactor effluent vapor stream from an interchanger or from a methanol synthesis reactor of the methanol production plant, wherein the cooler is preferably a tube and shell heat exchanger and comprises cooling tubes for cooling the methanol synthesis reactor effluent vapor stream, a shell side for passing of a fluid cooling medium, a tube sheet for separating the cooling tubes from the shell side; and spraying, using a recirculation pump connected to a spraying device, a liquid condensate received from a methanol synthesis loop onto the tube sheet of the cooler which enables direct contact of the liquid condensate with the methanol synthesis reactor effluent vapor stream and cools the methanol synthesis reactor effluent vapor stream.

Optionally, according to an aspect of the invention, the liquid condensate spray cools metal surfaces of the cooler. The cooling of the metal surfaces relaxes the constraint of the material and improves the efficiency of the cooler.

Optionally, according to an aspect of the invention, the liquid condensate comprises a stabilized crude methanol, a product methanol, or a wastewater obtained from the metha-
nol synthesis loop. The liquid condensate comprising the
stabilized crude methanol, the product methanol, or the
wastewater obtained from the methanol synthesis loop is
cooled and used directly with no additional cooling equip-
ment, for example an air cooler.

Optionally, according to an aspect of the invention, the
liquid condensate is cooled to a temperature below about 50
degrees Celsius, more preferably below about 40 degrees
Celsius. Experiments and/or calculation data have shown
this temperatures to allow a safe and reliable condensation
of the major part of the crude or raw methanol produced in
the methanol synthesis reactor, while keeping the energy
requirements at a tolerable level.

Optionally, according to an aspect of the invention, the
spraying device is arranged at the inlet of the cooler. This
allows a direct contact of the liquid condensate with the
methanol synthesis reactor effluent vapor stream and thus
cools the methanol synthesis reactor effluent vapor stream
very effectively.

Optionally, according to an aspect of the invention, a
mixture temperature of the liquid condensate and methanol
synthesis reactor effluent vapor is below about 100 degrees
Celsius, preferably below about 90 degrees Celsius. By
lowering the mixture temperature to below these upper
values, corrosion of the cooler internals and the downstream
equipment is effectively prevented, especially when chlo-
rides are present.

Optionally, according to an aspect of the invention, the
method comprises separating a liquid condensate stream and
a residual gas stream from the cooled methanol synthesis
reactor effluent vapor stream. Such configuration has advan-
tages for small capacity plants because the vapor-liquid
separator is also eliminated as a separate equipment posi-
tion. The liquid condensate stream comprises a raw metha-
nol product in a mix with water and impurities. The residual
gas is unreacted syngas that may comprise hydrogen, carbon
monoxide, carbon dioxide, methane, ethane, and dimethyl
ether.

Optionally, according to an aspect of the invention, the
method comprises separating a liquid condensate stream and
a residual gas stream from the cooled methanol synthesis
reactor effluent vapor stream. Such integration of vapor-
liquid separator in the cooler has advantages for small
capacity plants because the vapor-liquid separator is also
eliminated as a separate equipment position.

An example embodiment illustrates the principle for a 250
tons/day capacity methanol plant. The synthesis gas is
produced using an autothermal reformer (ATR). The Stoi-
chiometric Number SN equals 2.65, the Recycle Ratio RR
equals 2.1. The amount of crude methanol produced at this
scale is 14.6 tons/hours (t/h). The base case has an exit of the
interchanger at approximately 117 degrees Celsius (° C.)
with a total volumetric flow rate of 1830 cubic meter per
hour (m3/h). High temperature would lead to difficulties on
the cooling water side of the cooler. Implementing the
recirculation flow using the recirculation pump connected to
a nozzle as spraying device that sprays into the cooler inlet,
in the amount of 40 t/h, lowers the stream inlet temperature
to below 100° C., relaxing the constraint of the material. A
consequence is to also lower the volumetric flow rate of the
cooler inlet stream.

| Cooler Inlet Temperature ° C. | Cooler Inlet Flow m3/h | Recirculation Spray @ 40 C. t/h |
|---|---|---|
| 117.2 | 1830 | 0 |
| 98.9 | 1750 | 40 |
| 81.9 | 1724 | 100 |

A 40 t/h pump with low head requirements is a small piece
of equipment compared to the deletion of an air cooler. The
cooler has the same duty as the previous. With lower inlet
temperature, the area required will increase because of lower
logarithmic mean temperature difference (LMTD). How-
ever, the lower pressure drop of the exchanger leads to
savings in compression costs. The 100 t/h pump is a more
significant equipment item but still compares favorably to
the deletion of an air cooler.

Embodiments of the present disclosure substantially
eliminate or at least partially address the aforementioned
technical drawbacks in existing technologies in providing a
system and method for cooling a methanol reactor effluent
vapor stream in a small-scale methanol production plant
where the capital costs are dominant in determining the
overall economics.

FIG. 1 is a schematic illustration of a single-stage metha-
nol synthesis system 100 according to the prior art, but
without an air cooler, for methanol production. The single-
stage methanol synthesis system 100 includes a steam drum
102, a water-cooled methanol synthesis reactor 104, a
methanol interchanger (heat exchanger) 108, a final cooler
110, a methanol separator 112, a recycle gas compressor 116,
and a synthesis gas compressor 118. Liquid water flows
down from the steam drum 102 to a cooling jacket of the
water-cooled methanol reactor 104. The heat from the
reaction boils part of the water. A vapor-liquid mixture from
the water-cooled methanol reactor is returned to the steam
drum 102 for separating the vapor and liquid. Steam leaves
the steam drum 102 and liquid is retained in the steam drum
102 for additional cooling. Methanol reaction products from
the water-cooled methanol synthesis reactor 104 are passed
into the final cooler 110 for cooling after passing through the
methanol interchanger 108. The final cooler 110 includes a
cooling water supply (CWS) and cooling water return
(CWR) for cooling the reaction products from the water-
cooled methanol synthesis reactor 104. The cooled methanol
reaction products from the final cooler 110 are passed into
the methanol separator 112 where crude methanol is sepa-
rated as liquid from uncondensed vapor (residual vapor or
gas). A first portion of uncondensed vapor from the methanol
separator 112 after separating crude methanol becomes
purge gas and is used directly as fuel, e. g. in the synthesis
gas production plant. The remaining portion of uncondensed
vapor is compressed for recycle using the recycle gas
compressor 116. The purge and recycle gases comprise
unreacted gases and gaseous products such as hydrogen,
carbon monoxide (CO), carbon dioxide (CO$_2$), methane,
ethane, and dimethyl ether. A make-up gas composed of CO$_2$
and/or CO and also hydrogen is compressed with the syn-
thesis gas compressor 118 and mixed with the recycle gas
and supplied into the water-cooled methanol synthesis reac-
tor 104 through the methanol interchanger 108.

The omission of the air cooler in the flowsheet of FIG. 1
may result in a temperature of 120° C. or more for an inlet
gas to the cooler 108. Such a temperature is higher than
typically allowed for process-compatible steel metallurgies
in cooling water service where chlorides are present. Further, high metal surface temperatures can result in a break-down of the cooling water treatment chemicals and give rise to corrosion on a process side and/or fouling on a cooling waterside. For example, when chlorides are present, such temperatures can cause corrosion and fouling on the cooling water side of the cooler. Chloride content when using stainless steel can cause stress corrosion cracking. Using higher-grade metallurgy or a lower chloride content can avoid the corrosion problem, but then the equipment or the cooling water supply becomes more expensive. Even in this case, the cooling water chemistry may still cause fouling in an exchanger even without corrosion.

Figure 2:
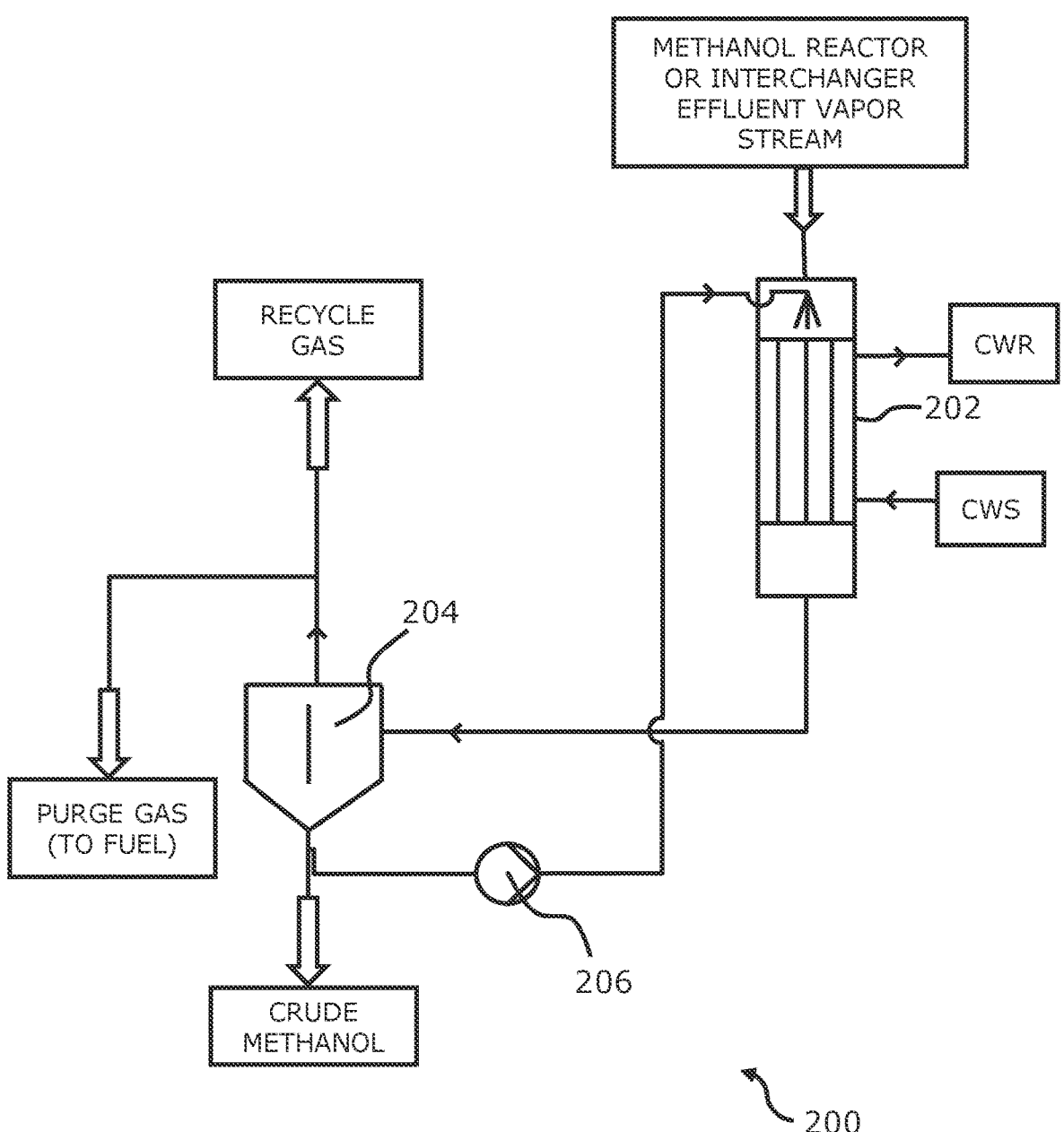
FIG. 2 is a schematic illustration of an embodiment of the invention, comprising a cooling system integrated with a methanol production plant for cooling a methanol synthesis reactor effluent vapor stream according to an embodiment of the present disclosure.

FIG. 2 is a schematic illustration of a cooling system 200 integrated with a methanol production plant for cooling a methanol synthesis reactor effluent vapor stream according to an embodiment of the present disclosure. The cooling system 200 includes a cooler 202, a vapor-liquid separator 204, a recirculation pump 206. The cooler 202 receives the methanol reactor effluent vapor stream from a methanol interchanger or a methanol synthesis reactor of the methanol production plant. The cooler 202 includes a cooling water supply (CWS) and a cooling water return (CWR) for cooling the methanol reactor effluent vapor stream from the metha-nol interchanger or the methanol reactor. The cooled metha-nol synthesis reactor effluent vapor stream from the cooler 202 is directed into the liquid-vapor separator 204 where crude methanol and uncondensed vapors (residual vapor or gas) are separated. A first portion of uncondensed vapor from the vapor-liquid separator 204 after separating crude methanol becomes purge gas and is used directly as fuel, e. g. in the synthesis gas production plant, and the remaining portion of uncondensed vapor is compressed using a recycle gas compressor and used as a recycle gas. The purge gas comprises unreacted gases and gaseous products such as hydrogen, carbon monoxide (CO), carbon dioxide ($CO_2$), methane, ethane, and dimethyl ether. A portion of crude methanol from the liquid-vapor separator 204 is recirculated through the recirculation pump 206 and sprayed back, by means of a spraying device, e. g. a nozzle, onto a cooling inlet and a tube sheet of the cooler 202. The recirculated crude methanol has an effect of direct-contact cooling of the incoming methanol reactor effluent vapor stream.

Figure 3:
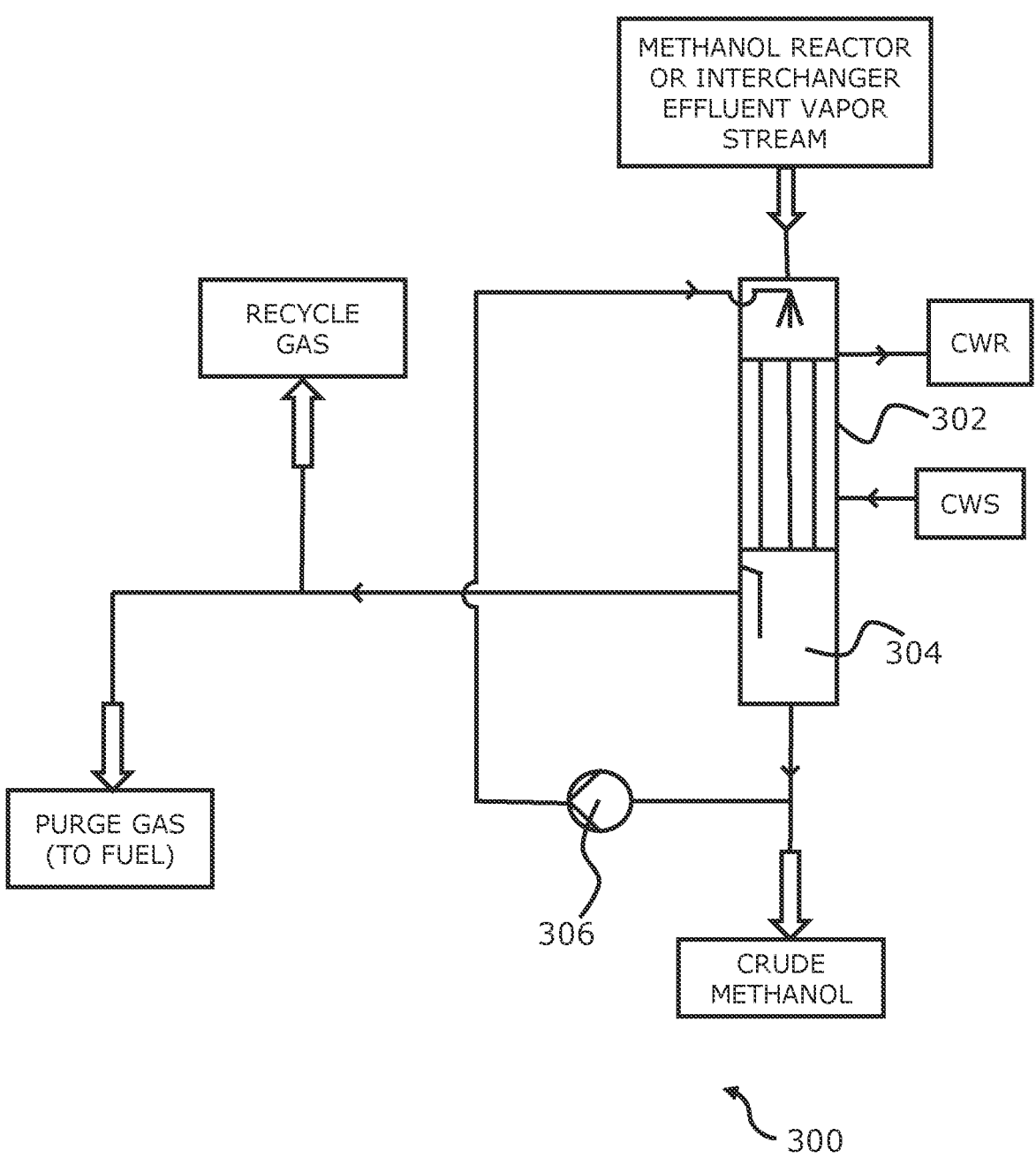
FIG. 3 is a schematic illustration of an embodiment of the invention, comprising a cooling system integrated with a methanol production plant cooler comprising an integrated vapor-liquid separator in the cooler according to an embodiment of the present disclosure.

FIG. 3 is a schematic illustration of a cooling system 300 integrated with a methanol production plant cooler compris-ing an integrated vapor-liquid separator 304 in the cooler 302 according to an embodiment of the present disclosure. The cooling system 300 includes an integrated vapor-liquid separator 304 in the cooler 302 and a recirculation pump 306. The cooler 302 receives the methanol reactor effluent vapor stream from a methanol interchanger or a methanol synthesis reactor of the methanol production plant. The cooler 302 includes a cooling water supply (CWS) and a cooling water return (CWR) for cooling the methanol reac-tor effluent vapor stream. The integrated vapor-liquid sepa-rator 304 in the cooler 302 is configured to separate crude methanol and uncondensed vapor (residual vapor or gas) from the cooled methanol synthesis reactor effluent vapor stream. A first portion of the uncondensed vapor from the integrated vapor-liquid separator 304 becomes purge gas and is used directly as fuel, e. g. in the synthesis gas production plant, and the remaining portion is compressed using a recycle gas compressor and used as a recycle gas. The uncondensed vapor comprises unreacted gases and gaseous products such as hydrogen, carbon monoxide (CO), carbon dioxide ($CO_2$), methane, ethane, and dimethyl ether. A portion of crude methanol from the integrated vapor-liquid separator 304 is recirculated through the recirculapump 306 and sprayed back, by means of a spraying device, e. g. a nozzle, onto a cooling inlet and a tube sheet of the cooler 302. The recirculated crude methanol has an effect of direct-contact cooling of the incoming methanol reactor effluent vapor stream.

Modifications to embodiments of the present disclosure described in the foregoing are possible without departing from the scope of the present disclosure as defined by the accompanying claims. Expressions such as "including", "comprising", "incorporating", "have", "is" used to describe, and claim the present disclosure are intended to be construed in a non-exclusive manner, namely allowing for items, components or elements not explicitly described also to be present. Reference to the singular is also to be construed to relate to the plural.

While the invention has been described in conjunction with specific embodiments thereof, it is evident that many alternatives, modifications, and variations will be apparent to those skilled in the art in light of the foregoing descrip-tion. Accordingly, it is intended to embrace all such alter-natives, modifications, and variations as fall within the spirit and broad scope of the appended claims. The present inven-tion may suitably comprise, consist or consist essentially of the elements disclosed and may be practiced in the absence of an element not disclosed. Furthermore, if there is lan-guage referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be addition-ally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circum-stance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

LIST OF REFERENCE NUMERALS

100—Single-stage methanol synthesis system
102—Steam drum
104—Water-cooled methanol synthesis reactor
108—Methanol interchanger
110—Final cooler
112—Methanol separator
116—Recycle gas compressor
118—Synthesis gas compressor
200—Cooling system
202—Cooler
204—Vapor-liquid separator
206—Recirculation pump 300—Cooling system
302—Cooler
304—Integrated vapor-liquid separator
306—Recirculation pump

The invention claimed is:

1. A cooling system for cooling a methanol synthesis reactor effluent vapor stream in a methanol production plant, wherein the cooling system is integrated with the methanol production plant, wherein the cooling system comprises:

a cooler, the cooler comprising a tube and shell heat exchanger, comprising cooling tubes for cooling the methanol synthesis reactor effluent vapor stream, a shell side for passing of a fluid cooling medium, a tube sheet for separating the cooling tubes from the shell side, and an inlet that receives the methanol synthesis reactor effluent vapor stream from an interchanger or from a methanol synthesis reactor of the methanol production plant; and a recirculation pump connected to a spraying device that is configured to spray a liquid condensate received from a methanol synthesis loop onto the tube sheet of the cooler which enables direct contact of the liquid condensate with the methanol synthesis reactor effluent vapor stream and cools the methanol synthesis reactor effluent vapor stream, wherein the cooling system further comprises a vapor-liquid separator for separating a liquid condensate stream and a residual gas stream from the cooled methanol synthesis reactor effluent vapor stream.

2. The cooling system according to claim 1, wherein the liquid condensate spray is configured to cool metal surfaces of the cooler.

3. The cooling system according to claim 1, wherein the liquid condensate comprises a stabilized crude methanol, a product methanol, or a wastewater obtained from the methanol synthesis loop.

4. The cooling system according to claim 1, wherein the liquid condensate is cooled to a temperature below about 50 degrees Celsius.

5. The cooling system according to claim 1, wherein the spraying device is arranged at the inlet of the cooler.

6. The cooling system according to claim 1, wherein a mixture temperature of the sprayed liquid condensate and methanol synthesis reactor effluent vapor is below about 100 degrees Celsius.

7. The cooling system according to claim 1, wherein the cooling system does not comprise an air cooler.

8. A method for cooling a methanol synthesis reactor effluent vapor stream in a methanol production plant, wherein the method comprises the steps of:

a. receiving, using an inlet of a cooler, the methanol synthesis reactor effluent vapor stream from an interchanger or from a methanol synthesis reactor of the methanol production plant; and b. spraying, using a recirculation pump connected to a spraying device, a liquid condensate received from a methanol synthesis loop onto the tube sheet of the cooler which enables direct contact of the liquid condensate with the methanol synthesis reactor effluent vapor stream and cools the methanol synthesis reactor effluent vapor stream.

9. The method according to claim 8, wherein the liquid condensate spray cools metal surfaces of the cooler.

10. The method according to claim 8, wherein the liquid condensate comprises a stabilized crude methanol, a product methanol, or a wastewater obtained from the methanol synthesis loop.

11. The method according to claim 8, wherein the liquid condensate is cooled to a temperature below about 50 degrees Celsius.

12. The method according to claim 8, wherein the spraying device is arranged at the inlet of the cooler.

13. The method according to claim 8, wherein a mixture temperature of the sprayed liquid condensate and methanol synthesis reactor effluent vapor is below about 100 degrees Celsius.

14. The method according to claim 8, wherein the method comprises separating, using a vapor-liquid separator, a liquid condensate stream and a residual gas stream from the cooled methanol synthesis reactor effluent vapor stream.

15. The method according to claim 14, wherein the method comprises recycling a part of the liquid condensate stream to the spraying device and discharging at least a part of the residual gas stream as purge stream.

16. The method according to claim 8, wherein the method comprises integrating a vapor-liquid separator in the cooler for separating a liquid condensate stream and a residual gas stream from the cooled methanol synthesis reactor effluent vapor stream.

17. The method according to claim 16, wherein the method comprises recycling a part of the liquid condensate stream to the spraying device and discharging at least a part of the residual gas stream as purge stream.

18. The method according to claim 8, wherein the cooler is a tube and shell heat exchanger and comprises cooling tubes for cooling the methanol reactor effluent vapor stream, a shell side for passing of a fluid cooling medium, a tube sheet for separating the cooling tubes from the shell side.

* * * * *